United States Patent [19]

Platz et al.

[11] 4,176,137

[45] Nov. 27, 1979

[54] MANUFACTURE OF CARBOXYLIC ACID AMIDES

[75] Inventors: Rolf Platz, Mannheim; Toni Dockner, Meckenheim; Jürgen Heners, Lingen; Herbert Krüg, Ludwigshafen, all of Fed. Rep. of Germany

[73] Assignee: BASF Aktiengesellschaft, Fed. Rep. of Germany

[21] Appl. No.: 959,733

[22] Filed: Nov. 13, 1978

[30] Foreign Application Priority Data

Nov. 17, 1977 [DE] Fed. Rep. of Germany ....... 2751236

[51] Int. Cl.$^2$ ............................................ C07C 102/08
[52] U.S. Cl. ........................... 260/561 N; 260/557 R; 260/558 R; 260/561 R; 252/457
[58] Field of Search ........... 260/561 N, 557 R, 558 R, 260/561 R; 252/457

[56] References Cited

U.S. PATENT DOCUMENTS

| | | | |
|---|---|---|---|
| 1,738,971 | 12/1929 | Storch | 252/457 |
| 3,767,706 | 10/1973 | Haberman et al. | 260/561 R |
| 3,928,439 | 12/1975 | Dockner et al. | 260/557 R |
| 3,994,973 | 11/1976 | Haberman et al. | 260/561 N |
| 4,036,879 | 7/1977 | Haberman | 260/561 N |
| 4,040,980 | 8/1977 | Matsuda | 260/561 N |
| 4,056,565 | 11/1977 | Matsuda | 260/561 N |
| 4,076,747 | 2/1978 | Matsuda et al. | 260/561 N |

*Primary Examiner*—Arthur P. Demers
*Attorney, Agent, or Firm*—Keil & Witherspoon

[57] ABSTRACT

A process for the manufacture of carboxylic acid amides by addition reaction of water with nitriles in the presence of a catalyst which contains copper and magnesium silicate and has been treated with a reducing gas, to which catalyst cement of a certain particle size has been admixed. The amides obtainable by the process are starting materials for the manufacture of solvents, flocculants, wetting agents, pesticides, crop protection agents, textile assistants, e.g. brighteners, water repellent agents, foam stabilizers and detergents.

16 Claims, No Drawings

MANUFACTURE OF CARBOXYLIC ACID AMIDES

The present invention relates to a process for the manufacture of carboxylic acid amides by addition reaction of water with nitriles in the presence of a catalyst which contains copper and magnesium silicate and has been treated with a reducing gas, to which catalyst cement of a certain particle size has been admixed.

U.S. Pat. No. 3,381,034 discloses that carboxylic acid amides can be manufactured from nitriles by addition reaction with water in the presence of copper-(II) and copper-(I) salts, and states that elementary copper may also be present. The yield of end product is unsatisfactory.

German Laid-Open Application DOS No. 2,001,903 teaches that reduced copper oxide, reduced copper/chromium oxide or reduced copper/molybdenum oxide, or corresponding mixtures, are catalysts for this reaction. The catalysts described in the Examples have insufficient selectivity when used for the industrially important addition reaction of water with acrylonitrile and methacrylonitrile. Example 3 shows that at the beginning of the reaction the yield and conversion are only about 50%; 30% of the converted nitrile appears as $\beta$-hydroxypropionitrile. Only after a very long reaction time does the conversion rise to 90% or more. On the other hand, Example 7 shows that the activity of the reduced oxide decreases after 1,400 hours and then the yield achieved is only 90% of theory. Even the presence of stabilizers in the form of barium compounds, as illustrated in Example 5, does not give satisfactory results; the conversion is 73%, falling to 43%, and the yield is 59%, only rising in the course of the reaction to 84%. The by-products, some of which are present in substantial amounts, can only be separated off by involved methods, if at all.

German Laid-Open Application DOS No. 2,036,126 describes a process for the manufacture of an amide by a catalytic addition reaction of water with a nitrile, eg. acrylonitrile and methacrylonitrile. Metal-containing catalysts, eg. Raney copper, Ullmann copper, reduced copper catalysts, copper on a carrier, silver, gold, cobalt, nickel, palladium and platinum, are mentioned. The copper catalysts referred to in Examples 1 to 10, eg. Raney copper, reduced copper oxide, Ullmann copper and copper on an asbestos carrier, give very low conversions and hence dilute acrylamide solutions. The period for which the activity of the catalyst lasts is not stated. Where Raney copper, which is relatively expensive and troublesome to produce, is used as the catalyst, the process is unsatisfactory in respect of economics, simplicity of operation and handling of the catalyst; Raney copper has a short life and the regeneration of such catalysts is troublesome. Moreover, German Laid-Open Application DOS No. 2,164,186 discloses that all these copper catalysts rapidly become deactivated and must be regenerated with hydrogen at an elevated temperature.

German Laid-Open Application DOS No. 2,320,060 relates to a process for the manufacture of carboxylic acid amides by addition reaction of water with nitriles in the presence of a copper-containing catalyst, wherein the reaction is carried out with a catalyst which contains copper and a magnesium silicate produced in the presence of a copper compound by precipitation of a magnesium compound with an alkali metal silicate, the catalyst being treated with a reducing gas at an elevated temperature.

We have found that the process of German Laid-Open Application DOS No. 2,320,060 can be improved further, if the magnesium silicate prepared as described above and separated from the precipitation medium is mixed with from 3 to 50 percent by weight, based on magnesium silicate, of a cement having a particle size of from 1 to 100 micrometers.

Where acrylonitrile is used, the reaction may be represented by the following equation:

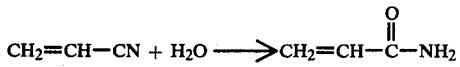

Compared to the conventional processes, the process of the invention gives a large number of carboxylic acid amides more simply and more economically, in good yield and high purity, and with better space-time yield, based on the total amount of copper in the catalyst, on sustained operation. The end product is in most cases obtained in such a pure form that it can immediately be processed further. Troublesome purification operations are avoided. The high selectivity of the catalyst and its long life permit longer operating times, especially on an industrial scale, and avoid frequent regeneration of the catalyst. Furthermore, the catalyst can be regenerated more simply and more rapidly. Metals which are expensive and difficult to obtain are not used. The catalyst according to the invention is not a supported catalyst with, for example, silicon dioxide or magnesium oxide acting as the carrier; in the catalyst, the magnesium or magnesium oxide and magnesium silicate make a substantial contribution to the catalytic properties. If copper oxide applied to a carrier is reduced with hydrogen, red copper is formed; if the catalyst according to the invention is reduced, black copper is formed. The catalyst according to the invention gives substantially higher space-time yields and higher selectivities, for example virtually 100 percent yield of acrylamide. A yield as high as that obtained by the process according to the invention is very important, since impurities in acrylamide can only be removed with difficulty, if at all.

Compared to the process described in German Laid-Open Application DOS No. 2,320,060, the process according to the invention can be carried out for substantially longer operating periods, particularly on an industrial scale. The catalyst is more easily moldable, particularly into shapes such as tablets, pills and extrudates, and retains its shape under the reaction conditions, particularly in the presence of water, during sustained operation. Even after having been used for more than 1,000–1,500 hours in an aqueous phase, at a high flow rate of reactants through the reactor, catalysts in, for example, tablet shape do not disintegrate; a constant loss of catalyst particles carried away as a fine suspension accordingly does not occur. Blockages of the reactor by such particles, which cause the pressure in the reactor to rise with increasing length of operation and finally make it necessary to change the catalyst, are avoided. All these advantageous characteristics of the process according to the invention are surprising since it would have been expected that on admixture of cement—which hardens when wetted with water—sticking together, hardening and shrinkage of the porous catalyst material would occur, accompanied, during the reaction, by a rapid reduction in the catalytic surface area, especially the inner surface area, a decrease in the pore size and number of pores and a correspondin decrease in yield, reduced catalyst selectivity, more frequent catalyst changes and reduced operating times. Surprisingly, the high yield of the process according to the invention remains virtually constant over the entire operating period.

Suitable starting materials are aliphatic, cycloaliphatic, araliphatic and aromatic mononitriles, dinitriles and polynitriles. Preferred starting materials are those of the formula $$R(-CN)_x \qquad \text{I}$$

and accordingly preferred end products are those of the formula $$R(-\overset{O}{\underset{\|}{C}}-NH_2)_x \qquad \text{II}$$

where X is 2 or especially 1 and R is alkyl of 1 to 6 carbon atoms, alkylene of 1 to 6, especially of 2 to 6, carbon atoms, alkenyl or alkenylene each of 2 to 6 carbon atoms, cycloalkyl or cycloalkylene of 5 or 6 carbon atoms, aralkyl or aralkylene of 7 to 12 carbon atoms, phenyl, phenylene, naphthyl or naphthylene. The above radicals may also be substituted by groups which are inert under the reaction conditions, eg. alkyl or alkoxy, each of 1 to 4 carbon atoms.

Examples of suitable starting materials are acetonitrile, propionitrile, cyclohexanecarboxylic acid nitrile, adipodinitrile, acrylonitrile, methacrylonitrile, crotononitrile, β-phenylacrylonitrile, benzonitrile p-toluylnitrile, β-naphthoic acid nitrile, phthalodinitrile, terephthalodinitrile, isophthalodinitrile, butyronitrile, maleodinitrile, glutarodinitrile, succinodinitrile, valeronitrile, capronitrile, fumarodinitrile, β-phenylacetonitrile and p-ethoxybenzonitrile.

The starting material can be reacted with a stoichiometric amount of water or with an excess; an advantageous ratio is from 1 to 50 moles of water per nitrile group of one mole of the starting material. The reaction is as a rule carried out at from 50° to 150° C., preferably from 60° to 110° C., under atmospheric or superatmospheric pressure, continuously or batchwise.

The catalyst essentially contains non-ionized copper which is either initially introduced, for example in the form of freshly reduced copper, into the magnesium silicate before the latter is subjected to its reductive treatment with reducing gases, or, more advantageously, is only formed from the copper compounds during the treatment. Advantageously, the copper originates from copper compounds which are present during precipitation of the magnesium silicate and are converted to the non-ionized form by the reductive treatment. In addition to the main amount of non-ionized copper, the treated catalyst may advantageously still contain from 0.001 to 30, preferably from 0.01 to 20, especially from 0.1 to 10, percent by weight, based on total copper, of monovalent and divalent copper, for example in the form of the original copper compound or of a compound formed during the treatment, eg. copper silicate. In general, suitable amounts are from 50 to 100, especially from 70 to 80, percent by weight of total copper, based on the amount of weight of magnesium silicate contained in the catalyst, and from 0.5 to 2, especially from 1 to 1.5, moles of starting nitrile, per gram atom of magnesium contained in the catalyst.

Examples of suitable copper compounds are the nitrate, sulfate, chloride, oxide, hydroxide, tartrate, acetate, oxalate and cyanide, cuprites such as sodium cuprite, and the bromide, iodide, nitrite or carbonate of monovalent or, advantageously, of divalent copper.

The magnesium silicate is produced in the presence of a copper compound, advantageously the copper compound which provides the non-ionized copper, by precipitating a magnesium compound with an alkali metal silicate, advantageously a potassium silicate or sodium silicate, as a rule in an aqueous precipitation medium, advantageously using a ratio of from 1 to 5 moles of alkali metal silicate per mole of magnesium compound. Suitable magnesium compounds are magnesium nitrate, sulfate, chloride, tartrate, acetate, oxalate, bromide, iodide and nitrite. The precipitation is advantageously carried out at from 15° to 50° C. The copper compound may in part be suspended in the precipitation medium.

The catalyst can also contain small amounts of zinc, cadmium, chromium, molybdenum, tungsten, vanadium, uranium, titanium and/or thorium in the form of the metals, or, advantageously, of appropriate compounds. Advantageous amounts of added metals are from 1 to 30, especially from 1 to 10, percent by weight, based on the amount by weight of magnesium contained in the catalyst. Suitable compounds to use are the nitrates, sulfates, chlorides, tartrates, acetates, oxalates, bromides, iodides and nitrites of the above metals. As a rule, these compounds will already be present in the medium in which the magnesium compound is precipitated.

In a preferred embodiment, catalysts which are obtained by precipitating a magnesium compound in the presence of the copper compound, with or without the presence of one or more compounds of the additional metals, in an aqueous medium, using the method of catalyst manufacture described in German Pat. No. 869,052, are used. In some cases, it is advantageous if after washing and drying, the precipitated material is kneaded with a not excessively large amount of alkali metal silicate solution, advantageously from 5 to 20 percent by weight, based on the precipitated material, of a sodium silicate or potassium silicate solution of from 10 to 30 percent strength by weight, and, after again drying, preferably at not too high a temperature, for example at from about 15° to 30° C., the material is molded. The addition of excessive amounts of alkali metal silicate can, under certain circumstances, lead to undesirable side reactions, which is why it is frequently advantageous if the catalysts are treated only after molding, and then only briefly, with a dilute waterglass solution or one of the above solutions.

Advantageously, aqueous solutions, of from 10 to 50 percent strength by weight, of the above copper compounds, and magnesium compounds, with or without additional metal compounds, and aqueous solutions, of from 10 to 30 percent strength by weight, of the alkali metal silicate are mixed with one another at the above precipitation temperature, and the precipitation is carried out for from 1 to 60 minutes. The precipitate is then advantageously filtered off and washed with water, for example until the original anion associated with the copper cation, eg. the nitrate anion, has been removed. The precipitate can then be pre-dried at from 20° to 30° C., molded, for example to give tablets, spheres or extrudates, and then dried at from 50° to 70° C. In general, it is however more advantageous to dry the filtered-off precipitate, which may or may not have been washed, admix the cement and mold the mixture. The reducing treatment is advantageously carried out thereafter.

The catalyst thus obtained is treated continuously or batchwise with reducing gases at an elevated temperature, advantageously at from 100° to 230° C., preferably at from 180° to 230° C., under atmospheric or superatmospheric pressure. As a rule, hydrogen is used as the reducing gas. However, other reducing gases may also be employed, for example carbon monoxide, olefins, eg. ethylene or propylene, or gas mixtures, or purified or unpurified gaseous mixtures (industrial gas) which contain reducing gases such as hydrogen or carbon monoxide, eg. fuel gases such as illuminating gas, generator gases, producer gas, coal gas, blast furnace exit gas, partially burnt generator gases, water gases, oil gas, coke oven gas, town gases, synthesis gases, industrial propane or industrial butane. The treatment time is advantageously from 0.5 to 24 hours, preferably from 1 to 15 hours. Advantageously, the catalyst, after having been manufactured and dried, is first kept under nitrogen, preferably in a stream of nitrogen, at an elevated temperature, preferably at from 100° to 180° C. especially from 120° to 140° C., advantageously for from 0.5 to 3 hours. The reductive treatment is then carried out, preferably for from 0.5 to 24 hours using from 5 to 15 moles of hydrogen or the equivalent amount of reducing gas per kilogram of catalyst. In a preferred embodiment, increasing amounts of hydrogen are introduced into the stream of nitrogen used for the pretreatment, whilst at the same time raising the temperature to the treatment temperature, and the nitrogen feed is correspondingly reduced, so that, for example after from 6 to 20 hours, a gas stream which only contains the reducing gas, or only contains the amount of nitrogen usually present in this reducing gas, is being employed instead of the stream of pure nitrogen. After the reduction, the catalyst advantageously only contains from 0 to 1, preferably from 0 to 0.1, percent by weight, based on total copper, of copper in the form of copper oxide, from 0 to 49, preferably from 0.1 to 30, percent by weight of copper in the form of copper silicate and from 51 to 100, preferably from 70 to 100, percent by weight of copper in the form of non-ionized copper, these figures again being based on total copper.

The admixture of the cement and/or the molding process, for example the production of granules, cubes, cylinders, rings, stars and especially tablets, spheres, pills or extrudates from the catalyst composition take place at several points, or as a rule at one point only, in the sequence of operations entailed in the manufacture of the catalyst. An advantageous sequence is as follows: (a) precipitation, (b) suction-draining or filtration of the precipitate, (c) washing if appropriate, as a rule with water, advantageously at from 20° to 50° C., and (d) drying at from 10° to 100° C., preferably at from 15° to 75° C.

Whilst the catalyst can be molded before admixture of the cement, and the two operations can also be separated from one another by one or more other operations, the molding is as a rule advantageously carried out following the admixture of the cement. Advantageously, both these steps are carried out after drying the precipitate.

Cement, advantageously with mixing additives, is used at the admixture stage. For the purposes of the invention, cement means materials which fall under the definition of cements given in Ullmanns Encyklopädie der technischen Chemie, volume 19, pages 1–31. Examples of suitable cement are Portland cement, Portland blast-furnace slag cement, blast furnace cement, trass cement, sulfate slag cement, Ferrari cement, iron ore cement, bauxite cement, Suevit trass cement, trass blast furnace cement, shale cement, oil well cement, expanding cement and high-alumina cement. The composition of these cements is advantageously from 20 to 69 percent by weight of CaO, from 0.2 to 30 percent by weight of $SiO_2$, from 5 to 75 percent by weight of $Al_2O_3 + TiO_2$, from 0 to 8 percent by weight of $Fe_2O_3$ or FeO, from 0 to 2 percent by weight of $Mn_2O_3$ (MnO), from 0 to 3 percent by weight of alkali metal oxide, from 0.2 to 7 percent by weight of MgO and from 0 to 9 percent by weight of $SO_3$. Regarding the manufacture and properties of the above cements, reference may be made to Ullmann (loc. cit.).

Preferably, the catalyst material (magnesium silicate), before mixing with the cement, has a specific surface area of from 100 to 200, preferably from 120 to 170, $m^2/g$, a pore volume of from 0.3 to 1.0, preferably from 0.6 to 0.9, $cm^3/g$, and an average pore radius of from 200 to 800, preferably from 400 to 620, nanometers. The cement, before mixing with the silicate, preferably has a specific surface area of from 0.5 to 5, preferably from 0.8 to 2, $m^2/g$, a tap density of from 800 to 900 g/l, and a particle size of from 2 to 70, preferably from 2.5 to 50, especially from 3 to 30, micrometers; the finished molded catalyst, after reduction, preferably has a specific surface area of from 80 to 180, preferably from 100 to 170, $m^2/g$, a pore volume of from 0.19 to 0.3, preferably from 0.22 to 0.28 $cm^3/g$, and a particle size of from 100 to 400, preferably from 100 to 300, micrometers. Where necessary, the catalyst composition or cement can additionally be comminuted, for example by milling, in order to achieve the above values.

The mixing additive used is generally water, preferably in a water-cement weight ratio of from 0.4 to 1.5:1, especially from 0.8 to 1.3:1. Advantageously, graphite, talc and/or fatty acids, eg. stearic acid, advantageously in an amount of from 1 to 10, preferably from 1 to 5, percent by weight, based on cement, are used as further mixing additives, which act as lubricants during molding.

The cement is admixed in an amount of from 3 to 50, preferably from 5 to 20, percent by weight based on magnesium silicate. In this ratio, magnesium silicate is defined as the amount of $MgSiO_3$ which theoretically corresponds to the total amount of magnesium present during precipitation, regardless of whether the amount of magnesium silicate actually obtained differs from the maximum amount, or differs in structure from $MgSiO_3$.

The admixture is in general effected at from 10° to 50° C., preferably from 20° to 40° C., under atmospheric or superatmospheric pressure, continuously or batchwise. The process may for example be carried out as follows: a mixture of cement, water and any further additives is added to the catalyst composition after drying. Molding can then be carried out in a plurality of steps, eg. in 2 steps, or, advantageously, in a single step. Advantageously, molding is carried out at from 10° to 50° C., preferably—in the case of the one-step process—at from 15° to 30° C. The finished molding can advantageously be allowed to come into renewed contact with water, for example by leaving it in moist air at from 15° to 30° C. or by immersing it in water at from 15° to 30° C. Advantageously, the wet moldings are sealed in plastic film bags and kept therein for 4 days at room temperature. Thereafter, they are advantageously left to dry for 7 days in air at 20° C. Lastly, they are advantageously heated for 11 days at 50° C. Thereafter, the reductive treatment of the molding is advantageously carried out in the manner described above.

The reaction may be carried out as follows: the nitrile starting material and water, and the catalyst which has been prepared, and reduced, in the manner described above, are kept for from 1 to 4 hours at the reaction temperature. The end product is then isolated from the reaction mixture in the conventional manner, eg. by filtering, concentrating the filtrate and again filtering.

The carboxylic acid amides obtainable by the process of the invention are valuable starting materials for the manufacture of solvents, flocculants, crosslinking agents, pesticides, crop protection agents, textile assistants, eg. brighteners, water repellent agents, foam stabilizers and detergents. The amides of higher fatty acids are surfactants and brighteners. Unsaturated carboxylic acid amides, eg. acrylamide and methacrylamide, are well-known monomers for the production of plastics. Regarding the use of the amides, reference may be made to the above publications and to Ullmanns Encyklopädie der technischen Chemie, volume 14, pages 287 et seq. and supplementary volume, page 136.

In the Examples which follow, parts are by weight and bear the same relation to parts by volume as that of the kilogram to the liter.

EXAMPLE 1

(a) Preparation of the Catalyst

Aqueous 20 percent strength by weight solutions of 160 parts of copper nitrate, 100 parts of magnesium nitrate and 8 parts of chromium nitrate are mixed with one another and an aqueous 15 percent strength by weight solution of 200 parts of potassium silicate is then added at 20° C. The suspension formed is filtered and the filter residue is washed with water until the wash liquor no longer contains nitrate anions. The filter residue is dried for 5 hours at 40° C. The dried material (90 parts) is milled and mixed with 5 parts of cement and 15 parts of water at 20° C. Before this admixture, the filter residue has a specific surface area of 150 m$^2$/g, a pore volume of 0.90 cm$^3$/g and a pore radius of 610 nanometers. The cement, before admixture, has a specific surface area of 1 m$^2$/g and a tap density of 850 g/l. After mixing, the powder is molded at 20° C. under a pressure of 800 bar to give 5×3 mm tablets. The moldings are sealed wet in film bags and kept for 4 days at 20° C. Thereafter, they are allowed to dry in air for 7 days. The reductive treatment is started by heating the tablets in a stream of nitrogen for 60 minutes at 130° C. and 1 bar. A progressively increasing proportion of hydrogen is then added to the nitrogen. The entire nitrogen has been replaced by hydrogen within 2 hours, with the temperature rising at 220° C. The catalyst is then kept for 3 hours at 220° C. in a stream of pure hydrogen, after which it is cooled. The catalyst thus obtained (1,000 parts), which contains 300 parts of total copper, of which 299 parts are non-ionized copper, is used in the Examples which follow; it has a specific surface area of 135 m$^2$/g, a pore volume of 0.23 cm$^3$/g and an end-face breaking resistance of 25 bar.

(b) Reaction

The catalytic addition reaction with water is carried out continuously in a tubular reactor. The reactor has a length of 2 meters and a diameter of 50 millimeters and is filled with 1,000 parts of catalyst produced as described above. Per hour, 160 parts of oxygen-free acrylonitrile and 500 parts of oxygen-free water are introduced at the bottom of the reactor by means of metering pumps. The reaction temperature is kept at 70° C. The liquid reaction mixture is passed over a separator, a cooler and a further separator. After filtering, and concentrating the filtrate and filtering a second time, 7.76 parts of acrylonitrile and 22.1 parts of acrylamide of melting point 84.5° C. are obtained per hour. This corresponds to a conversion of 68 percent; the yield is virtually 100 percent.

EXAMPLE 2

The procedure described in Example 1 is followed, using a catalyst containing 10 parts of cement. The cement has a specific surface area of 2 m$^2$/g and a tap density of 850 g/l. The catalyst has a specific surface area of 125 m$^2$/g, a pore volume of 0.24 cm$^3$/g and an end-face breaking resistance of 65 kg/cm$^2$ of end-face. The tablets employed have retained their initial shape after 4,000 hours. After filtering and concentrating the filtrate and filtering a second time, 9.48 parts of acrylonitrile and 19.8 parts of acrylamide of melting point 84.5° C. are obtained per hour, corresponding to a conversion of 61 percent and a yield of >99% of theory.

EXAMPLE 3

The procedure described in Example 1 is followed, but a catalyst containing 20 parts of cement is used. The cement has a specific surface area of 2 m$^2$/g and a bulk density of from 800 to 900 g/l. The catalyst has a specific surface area of 100 m$^2$/g, a pore volume of 0.20 cm$^3$/g and an end-face breaking resistance of 81 bar. After 1,000 hours operation, the breaking resistance is 74 bar, falling to 68 bar after 4,000 operating hours. The catalyst employed retains its shape. After filtering and concentrating the filtrate and filtering a second time, 11.43 parts of acrylonitrile and 17.2 parts of acrylamide of melting point 84.5° C. are obtained per hour, corresponding to a conversion of 53 percent and a yield of >99% of theory.

EXAMPLE 4 (COMPARATIVE EXAMPLE)

The procedure followed is as described in Example 1, but a cement-free catalyst having an end-face breaking resistance of 20 bar is employed. The catalyst has a specific surface area of 150 m$^2$/g, a pore volume of 0.88 cm$^3$/g and a pore radius of 570 nanometers. After 1,000 hours operation, the breaking resistance is 16 bar, falling to 10 bar after 2,000 operating hours. After 3,000 hours, the greater part of the tablets introduced has disintegrated. After filtering and concentrating the filtrate and filtering a second time, 7.3 parts of acrylonitrile and 22.7 parts of acrylamide of melting point 84.5° C. are obtained per hour, corresponding to a conversion of 70 percent and a yield of >99% of theory.

TABLE

| Example | End-face breaking resistance (kg/cm² of end-face) | | | | Yield, % of theory |
| --- | --- | --- | --- | --- | --- |
| | after 1,000 hours | 2,000 hours | 3,000 hours | 4,000 hours | |
| 1 | 25 | 14 | 10% of the catalyst has disintegrated | — | greater than 99 |
| 2 | 65 | 58 | 53 | 50 | greater than 99 |
| 3 | 81 | 74 | 71 | 68 | greater than 99 |
| 4 (comparative experiment) | 20 | 10 | completely disintegrated | — | greater than 99 |

We claim:

1. A process for the manufacture of carboxylic acid amides by addition reaction of water with nitriles in the presence of a copper-containing catalyst, wherein the reaction is carried out with a catalyst which contains copper and a magnesium silicate produced in the presence of a copper compound by precipitation of a magnesium compound with an alkali metal silicate, the catalyst being treated with a reducing gas at an elevated temperature, and wherein the magnesium silicate prepared as described above and separated from the precipitation medium is mixed with from 3 to 50 percent by weight, based on magnesium silicate, of a cement having a particle size of from 1 to 100 micrometers.

2. A process as claimed in claim 1, wherein the reaction is carried out with a starting material of the formula $$R(-CN)_x$$

where x is 2 or 1 and R is alkyl of 1 to 6 carbon atoms, alkylene of 1 to 6 carbon atoms, alkenyl or alkenylene each of 2 to 6 carbon atoms, cycloalkyl or cycloalkylene of 5 or 6 carbon atoms, aralkyl or aralkylene of 7 to 12 carbon atoms, phenyl, phenylene, naphthyl or naphthylene, and the above radicals may in addition be substituted by groups which are inert under the reaction conditions.

3. A process as claimed in claim 1, wherein the reaction with water is carried out using a ratio of from 1 to 50 moles of water per nitrile group of one mole of the starting material.

4. A process as claimed in claim 1, wherein the reaction is carried out at from 50° to 150° C.

5. A process as claimed in claim 1, wherein the reaction is carried out at from 60° to 110° C.

6. A process as claimed in claim 1, wherein the reaction is carried out with from 50 to 100% by weight of total copper, based on the amount by weight of magnesium silicate contained in the catalyst.

7. A process as claimed in claim 1, wherein the reaction is carried out with from 0.5 to 2 moles of nitrile starting material per gram atom of magnesium contained in the catalyst.

8. A process as claimed in claim 1, wherein the reaction is carried out with from 1 to 30% by weight, based on the amount by weight of magnesium contained in the catalyst, of additional metal in the catalyst.

9. A process as claimed in claim 1, wherein the reaction is carried out with a catalyst which has been manufactured by mixing aqueous solutions, of from 10 to 50 percent strength by weight, of copper compounds, magnesium compounds and additional metal compounds, if any, and aqueous solutions, of from 10 to 30 percent strength by weight, of an alkali metal silicate at the above precipitation temperature, effecting the precipitation for from 1 to 60 minutes, and then filtering off the precipitate, washing it with water, pre-drying it at from 20° to 30° C., molding it, and then drying it at from 50° to 70° C.

10. A process as claimed in claim 1, wherein the reaction is carried out with a catalyst which after its preparation and drying is first kept under nitrogen at from 100° to 180° C. and is then treated with reducing gases from 100° to 230° C.

11. A process as claimed in claim 1, wherein the reaction is carried out with a catalyst which has been reduced with from 5 to 15 moles of hydrogen or a corresponding equivalent of another reducing gas per kilogram of catalyst.

12. A process as claimed in claim 1, wherein the reaction is carried out with a catalyst which contains from 0 to 1 percent by weight of copper in the form of copper oxide, from 0 to 49 percent by weight of copper in the form of copper silicate and from 51 to 100 percent by weight of copper in the form of non-ionized copper, the said percentages being based on total copper.

13. A process as claimed in claim 1, wherein the reaction is carried out with a catalyst obtained using a magnesium silicate which before mixing with the cement has a specific surface area of from 100 to 200 m²/g, a pore volume of from 0.3 to 1.0 cm³/g and an average pore radius of from 200 to 800 nanometers.

14. A process as claimed in claim 1, wherein the reaction is carried out with a catalyst obtained using a cement which before mixing with the magnesium silicate has a specific surface area of from 0.5 to 5 m²/g, a tap density of from 800 to 900 g/l and a particle size of from 2 to 70 micrometers.

15. A process as claimed in claim 1, wherein the reaction is carried out with a finished molded catalyst which after reduction has a specific surface area of from 80 to 180 m²/g, a pore volume of from 0.19 to 0.3 cm³/g and a particle size of from 100 to 400 micrometers.

16. A process as claimed in claim 1, wherein the reaction is carried out with a catalyst obtained using a cement in an amount of from 3 to 50 percent by weight, based on magnesium silicate.

* * * * *